United States Patent
Kim et al.

(10) Patent No.: US 8,314,082 B2
(45) Date of Patent: Nov. 20, 2012

(54) STILBENE DERIVATIVES FOR ADP-RIBOSYL CYCLASE INHIBITORS

(75) Inventors: Uh-Hyun Kim, Jeonbuk (KR); Ho-Jeong Kwon, Seoul (KR); Mie-Jae Im, Jeonbuk (KR); Seon-Young Kim, Jeonbuk (KR); Kwang-Hyun Park, Jeonbuk (KR); So-Young Rah, Jeonbuk (KR); Tae-Sik Nam, Seoul (KR); Byung-Ju Kim, Jeonbuk (KR); Gul Rukhsana, Jeonbuk (KR)

(73) Assignee: Industrial Cooperation Foundation Chonbuk National University, Jeollabuk-do (KR)

( * ) Notice: Subject to any disclaimer, the term of this patent is extended or adjusted under 35 U.S.C. 154(b) by 0 days.

(21) Appl. No.: 13/149,166

(22) Filed: May 31, 2011

(65) Prior Publication Data

US 2011/0281826 A1    Nov. 17, 2011

Related U.S. Application Data

(62) Division of application No. 12/520,391, filed as application No. PCT/KR2007/006921 on Dec. 28, 2007, now abandoned.

(30) Foreign Application Priority Data

Dec. 28, 2006    (KR) .......................... 10-2006-0135890

(51) Int. Cl.
*A61K 31/05*    (2006.01)
(52) U.S. Cl. ........................................................ 514/150
(58) Field of Classification Search .................. None
See application file for complete search history.

(56) References Cited

U.S. PATENT DOCUMENTS

| 3,152,038 | A | * | 10/1964 | Urbschat et al. | 514/150 |
| 4,055,567 | A |  | 10/1977 | Murtha |  |
| 4,683,241 | A |  | 7/1987 | Miyano et al. |  |
| 4,985,416 | A | * | 1/1991 | Teicher | 514/150 |
| 6,165,998 | A | * | 12/2000 | Wobbe et al. | 514/150 |
| 2005/0020595 | A1 |  | 1/2005 | Kalish et al. |  |
| 2007/0099826 | A1 | * | 5/2007 | Wong et al. | 514/12 |

FOREIGN PATENT DOCUMENTS

| WO | WO-0160774 | 2/2001 |
| WO | WO-2006113485 | 10/2006 |

OTHER PUBLICATIONS

Nam et al. Experimental and Molecular Medicine vol. 38(6):718-726 (2006).*
J. Trapp et al., "Adenosine Mimetics Inhibitors of NAD+-Dependent Histone Deacetylases, From Kinase to Sirtuin Inhibition," *Journal of Medical Chemistry*, 2006, vol. 49, pp. 7307-7316.
Ramesh Babu et al., *Journal of Crystal Growth*, 256 (2003) 387-392.

* cited by examiner

*Primary Examiner* — Kamal Saeed
*Assistant Examiner* — Nyeemah A Grazier
(74) *Attorney, Agent, or Firm* — Dickstein Shapiro LLP

(57) ABSTRACT

The present disclosure relates to bisphenyl compounds that are useful for inhibiting the ADP-ribosyl cyclase (ADPR-cyclase). More particularly, the disclosed compounds can be used for treatment and prevention of hypertension, hypertensive cardiac hypertrophy, diabetes, and diabetic nephropathy, in which pathogenesis ADPR-cyclase is involved. The compounds and compositions of the invention can be used for treatment and prevention of cardiovascular disease and related disease states, particularly, hypertension or diabetes related disorders, such as, hypertensive cardiac hypertrophy, diabetic nephropathy, and the like.

2 Claims, 3 Drawing Sheets

STILBENE DERIVATIVES FOR ADP-RIBOSYL CYCLASE INHIBITORS

CROSS REFERENCE TO RELATED APPLICATION

The present application is a divisional of Ser. No. 12/520,391, filed Oct. 27, 2009 now abandoned, which was a national stage application of PCT Application No. PCT/KR07/06921, filed Dec. 28, 2007, which claims priority to Korean Application No. 10-2006-0135890, filed Dec. 28, 2006, the entire disclosures of which are incorporated herein by reference.

TECHNICAL FIELD

The present disclosure relates to bisphenyl compounds that are useful for inhibit the ADP-ribosyl cyclase (ADPR-cyclase). More particularly, the disclosed compounds can be used for treatment and prevention of hypertension, hypertensive cardiac hypertrophy, diabetes, and diabetic nephropathy, in which pathogenesis ADPR-cyclase is involved.

BACKGROUND ART

ADP-ribosyl cyclase (ADPR-cyclase) is widely distributed and plays a critical role in regulation of intracellular $Ca^{2+}$ concentration ($[Ca^{2+}]_i$) via cyclic ADP-ribose (cADPR) production [Guse et al., Nature 1999(398):70-3; Galione et al., Sci STKE 2000(41):PE1; Lee, Curr. Mol. Med. 2004(4): 227-37]. The metabolite cADPR is known to increase $[Ca^{2+}]_i$ by releasing from intracellular $Ca^{2+}$ stores or by $Ca^{2+}$ influx through plasma membrane $Ca^{2+}$ channels from plants to mammals [Guse et al., Nature 1999(398):70-3; Galione et al., Sci STKE 2000(41):PE1; Lee, Annu. Rev. Pharmacol Toxicol. 2001(41):317-45; Partida-Sanchez et al., Nat. Med. 2001(7): 1209-16].

The homeostasis of intracellular $Ca^{2+}$ ($[Ca^{2+}]_i$) is essential for regulate of physiological functions. Moreover, calcium ions are ubiquitous and versatile signaling molecules, capable of decoding a variety of extracellular stimuli (hormones, neurotransmitters, growth factors, etc.) into markedly different intracellular actions, ranging from contraction to secretion, from proliferation or hypertrophy to cell death. The abnormal increase of $[Ca^{2+}]_i$ causes physiologic or pathophysiologic disorders, such as hypertension, hypertensive diabetes, obesity, ischemia, and renal dysfunction et al., [Resnick et al., Am. J. Hypertens. 1993(6): 123-34].

Angiotensin II (Ang II) plays a key role in the regulation of cardiovascular homeostasis. Acting on both the "content" and the "container" Ang II regulates blood volume and vascular resistance. The wide spectrum of Ang II target tissues includes the adrenals, kidney, brain, pituitary gland, vascular smooth muscle, and the sympathetic nervous system. Angiotensin is not only a blood-borne hormone that is produced and acts in the circulation but is also formed in many tissues such as brain, kidney, heart, and blood vessels [Gasparo et al., Pharmacol. Rev. 2000(52):415-72]. Recent studies report that Ang II induces ADPR-cyclase activation and production of cADPR [Fellner et al., Am. J. Physiol Renal Physiol. 2005 (288): F785-91; Higashida et al., Biochem. J. (2000)352:197-202].

ADPR-cyclase is present in brain, heart, kidney, arterial smooth muscle cells, and bone marrow cells [Hirata et al., FEBS Lett. (1994)356:244-8; de Toledo et al., Circ. Res. (2000)86:1153-9; Ceni et al., J. Biol. Chem. (2003)278:40670-8; Zielinska et al., Life Sci. (2004)74:1781-90; Xie et al., Biochem. Biophys. Res. Commun. (2005)330: 1290-8]. A number of studies indicate that ADPR-cyclase/CD38 is necessary for $Ca^{2+}$ sensitive biologic responses in which insulin secretion, obesity, neurodegeneration [Panfoli et al. Invest. Ophthalmol. Vis. Sci. (2007)48:978-84; Maria et al., FASEB J. (2007)21:3629-39; Duo et al., Nature (2007) 446:41-5].

A study with mice disrupted CD38 gene has demonstrated that formation of cADPR is not reduced greatly in mouse kidney, brain, and heart [Partida-Sanchez et al., Nat. Med. 2001(7): 1209-16], suggesting that ADPR-cyclases other than CD38 exist. However, the ADPR-cyclase(s) present in these tissues has not been cloned, and the cADPR antagonistic derivatives such as 8-Br-cADPR and 8-$NH_2$-cADPR do not distinguish the $Ca^{2+}$ signals induced by the unidentified ADPR-cyclase or CD38 [Walseth et al., Biochim. Biophys. Acta. (1993)1178:235-42].

The present invention provides available bisphenyl derivatives that inhibit specific ADPR-cyclase activity with high potency, but not CD38. These compounds that are thought to contribute to the prevention or treatment of various diseases, including hypertension and diabetic nephropathy.

DISCLOSURE OF INVENTION

Technical Problem

An object of the present invention is to provide novel ADPR-cyclase inhibitors, which are bisphenyl compounds. Theses molecules exhibit highly selective and specific inhibition effects in ADPR-cyclase activation.

This invention also provides that a small molecule ADPR-cyclase inhibitor can develop as therapeutic agents for the treatment and prevention of cardiovascular and renal disease, particularly, hypertension or hypertensive cardiac hypertrophy and diabetic or hypertensive nephropathy. Technical Solution.

The present invention provides specific ADPR-cyclase inhibitors, particularly, bisphenyl compound of Formula I.

Chemistry Figure 1

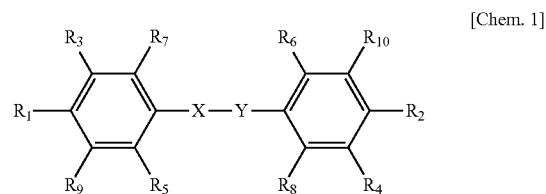

[Chem. 1]

wherein:

X and Y are selected from C and N;

$R_1$, $R_2$, $R_3$, $R_4$, $R_5$, $R_6$, $R_7$, $R_8$, $R_9$, and $R_{10}$ are each independently selected from hydrogen and hydroxyl;

X—Y is selected from a single bond or double bond;

and pharmaceutically acceptable composition, salts and hydrates thereof;

The term "pharmaceutically acceptable composition" as used herein refers to a composition comprising at least one compound as disclosed herein formulated together with one or more pharmaceutically acceptable carriers.

The term "pharmaceutically acceptable salt(s)" refers to salts of acidic or basic groups that may be present in compounds used in the present compositions. Compounds included in the present compositions that are basic in nature are capable of forming a wide variety of slats with various inorganic and organic acids. The acids that may be used to prepare pharmaceutically acceptable acid addition salts of such basic compounds are those that form non-toxic acid addition salts, i.e., slats containing pharmacologically acceptable anions.

Substituent around a carbon-carbon double bond or nitrogen-nitrogen double bond alternatively can be referred to as "cis" or "trans" where "cis" represents substituent on the same side of the double bond and "trans" represents substituent on opposite sides of the double bond.

The present disclosure also provides pharmaceutical compositions comprising compounds as disclosed herein formulated together with one or more pharmaceutically acceptable carriers. These formulations include those suitable for oral, rectal, topical, buccal, and parenteral, such as subcutaneous, intramuscular, intradermal, or intravenous, administration, although the most suitable form of administration in any given case will depend on the degree and severity of the condition being treated and on the nature of the particular compound being used.

The amount of active compound administered may be dependent on the subject being treated, the subject's weight, and the manner of administration and the judgment of prescribing physician. For example, a dosing schedule may involve the daily or semi-daily administration of the encapsulated compound at a perceived dosage of about 0.05 mg to about 35 mg, particularly, about 0.2 mg to about 25 mg.

The therapeutically effective amount of the compound of Formula I is sufficient to establish a concentration ranging from about 0.001 mM to about 100 mM, particularly, from about 0.1 mM to about 20 mM in mammals.

A therapeutically effective amount of a compound or composition disclosed herein can be measured by the therapeutic effectiveness of the compound. Compounds of the invention may be administered in a dose of about 1 mg/kg to about 50 mg/kg daily. However, the dosages may be varied depending upon the requirements of the patients, the severity of the condition being treated, and the compound being used.

In certain embodiments, the compounds of the invention are useful for treatment of diseases characterized by activated ADPR-cyclase and/or cADPR. The compounds and composition of the invention can be used to selective and specific inhibition of ADPR-cyclase. An activation of ADPR-cyclase leads to an increase of intracellular calcium levels, which are related on blood pressure overload and glucose homeostasis. Thus, the compounds of the invention may further be used to treatment and prevention of hypertension, diabetes, and diabetic nephropathy. Accordingly, the compounds and compositions of the invention can be used for treatment and prevention of cardiovascular disease and related disease states, particularly, hypertension or diabetes related disorders, such as, hypertensive cardiac hypertrophy, diabetic nephropathy, and the like.

Advantageous Effects

The compounds and compositions of the invention can be used for treatment and prevention of cardiovascular disease and related disease states, particularly, hypertension or diabetes related disorders, such as, hypertensive cardiac hypertrophy, diabetic nephropathy, and the like.

BRIEF DESCRIPTION OF THE DRAWINGS

FIGS. 1A and 1B are referred to as FIG. 1 herein.

FIGS. 2A and 2B are referred to as FIG. 2 herein.

FIGS. 3A and 3B are referred to as FIG. 3 herein.

FIGS. 4A and 4B are referred to as FIG. 4 herein.

BEST MODE FOR CARRYING OUT THE INVENTION

Example 1

Figure 1A:
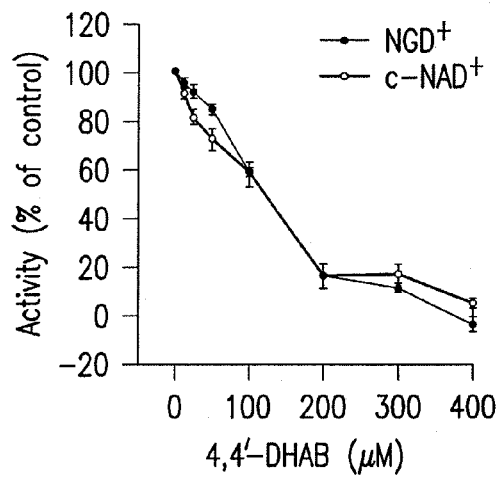
FIGS. 1A and 1B show the inhibition of rat kidney ADPR-cyclase that was incubated with 200 mM NGD$^+$ or e-NAD$^+$ in the presence of various concentrations of 4,4'-dihydrioxyazobenzene (DHAB) at 37° C. for 10 min and effects of DHAB on human CD38, rat brain, heart, spleen, and kidney ADPR-cyclase.
Figure 1B:
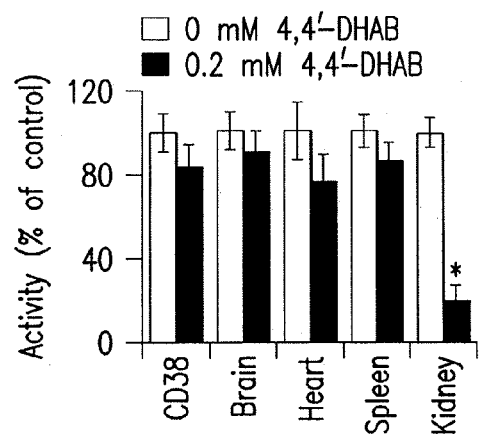

Assays for ADPR-Cyclase or cADPR-Hydrolase and Inhibition Effects of 4,4-DHAB in a Dose Dependent Manner Specific ADPR-cyclase activity was determined by measuring cyclic GDP-ribose (cGDPR) or etheno-ADP-ribose (e-cADPR) fluorometrically using NGD$^+$ or e-NAD$^+$ as a substrate [Greaff et al., Biochem. J. (2002)361:379-84]. Samples were incubated in the presence of 200 mM NGD$^+$ or e-NAD$^+$ with and without an appropriate agent in an assay buffer (25 mM HEPES, pH 7.4, 100 mM NaCl, and 0.1% Triton X-100) in a 50 ml-final volume. The reaction mixture was incubated at 37° C. for 10 min. The reaction was stopped by adding 50 ml trichloroacetic acid (10%). The samples were centrifuged at 21,000 g for 10 min and the supernatant (80 ml) was diluted with 920 ml of 100 mM sodium phosphate buffer (pH 7.2). Fluorescence of cGDPR or e-ADPR in the solution was determined at excitation/emission wavelengths of 297/410 nm (HITACHI F-2000 fluorescence spectrophotometer). cADPR-hydrolase activity was determined by incubating cADPR with ADPR-cyclase or CD38 at 37° C. for 20 min. Hydrolysis of cADPR was analyzed by high performance liquid chromatography as described (White et al., 2000). The results provided in FIG. 1 that 4,4'-DHAB was able to inhibit generation of cGDPR and e-ADPR from NGD$^+$ and e-NAD$^+$, respectively, by the kidney ADPR-cyclase in a concentration-dependent manner. These results suggest that the compound may bind to the active site of the enzyme. Half maximal inhibition (IC$_{50}$) of the enzyme activity was approximately 100 mM. CD38 and ADPR-cyclases purified partially from rat brain, heart, and spleen tissues were insensitive to 4,4'-DHAB at 200 mM.

MODE FOR THE INVENTION

Example 2

Measurement of Ang II-Mediated $[Ca^{2+}]_i$ Increase in MMCs

Changes in $[Ca^{2+}]_i$ in MMCs were determined as described previously [Kim et al., Exp. Mol. Med. (2006)38:535-45]. Briefly, MMCs cultured on confocal dishes for 48 h at a concentration of $10^4$ cells/dish were washed with Hank's balanced salt solution (HBSS) (2 mM CaCl$_2$, 145 mM NaCl, 5 mM KCl, 1 mM $MgCl_2$, 5 mM D-glucose, and 20 mM HEPES, pH 7.3) and then loaded with 5 mM Fluo 3-AM (Molecular Probe, Eugene, Oreg.). Changes in $Ca^{2+}$ fluorescence were determined at 488 nm/530 nm (excitation/emission) by air-cooled argon laser system. $[Ca^{2+}]_i$ was calculated using a $K_d$ of 325 nM for Fluo 3-AM by the method of Tsien et al. (1982). The results provided in FIG. 2 and Table 1.

Below table 1 corresponds to inhibitory potency of DAHB, DAHB analogs, and structurally similar compounds on $Ca^{2+}$ signal and cADPR production in response to Ang II.

TABLE 1

| Structure | Compound | $IC_{50}([Ca^{2+}]_i, uM)$ (means ± SEM) | $IC_{50}([CADPR]_i, uM)$ (means ± SEM) |
|---|---|---|---|
| 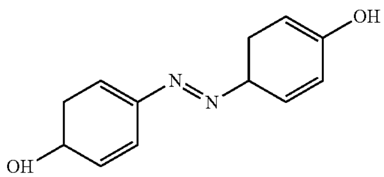 | 4,4'-Dihydroxy-azobenzene | 0.0025 ± 0.0002 | 0.0025 ± 0.0003 |
| 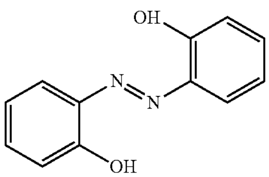 | 2,2'-Dihydroxy-azobenzene | 15 ± 1.5 | 16.5 ± 2.5 |
| 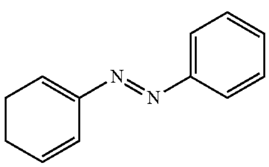 | Azobenzene | 10 ± 1.1 | 13 ± 2.1 |
| 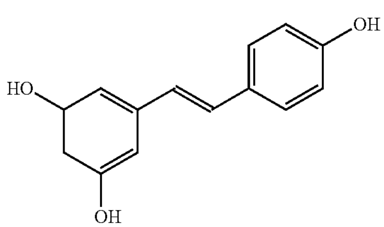 | Resveratol (3,5,4'-trihydroxy-trans-stilbene) | 5 ± 0.8 | 5.5 ± 0.5 |
| 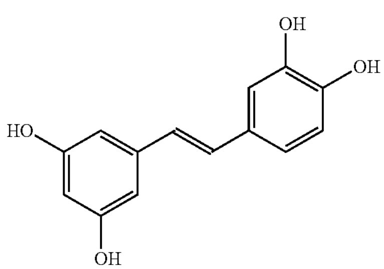 | Piceatannol (3,5,3',4'-tetrahydroxy-trans-stilbene) | 10 ± 1.7 | 8.9 ± 1.5 |

$IC_{50}$ of the compounds for cADPR production and the later sustained $Ca^{2+}$ signal induced by 150 nM Ang II was determined after incubation for 90 s ([c ADPR]$_i$) and 300 s ($[Ca^{2+}]_i$).

Figure 2A:
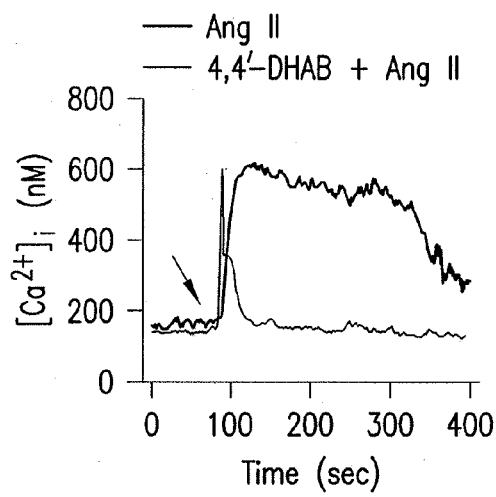
FIGS. 2A and 2B show the inhibition effects of 4,4'-DHAB on angiotensin II (Ang II) induced $[Ca^{2+}]_i$ increase and cADPR production in murine mesangial cells (MMCs).
Figure 2B:
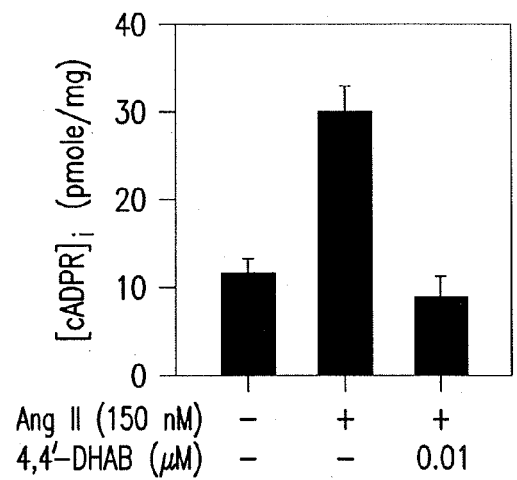

Ang II generates of long-lasting increase of $[Ca^{2+}]_i$, a burst $Ca^{2+}$ rise followed by a sustained $Ca^{2+}$ rise that was gradually decreased (FIG. 2). The sustained $Ca^{2+}$ signal, but not the initial burst $Ca^{2+}$ rise, was blocked by pretreatment with 4,4'-DHAB as a possible candidate inhibitor of ADPR-cyclase. $IC_{50}$ was approximately 2.5 nM (See the above Table 1).

Example 3

Measurement of Ang D-Mediated $[Ca^{2+}]_i$ Increase in Cardiomyocytes

Figure 3A:
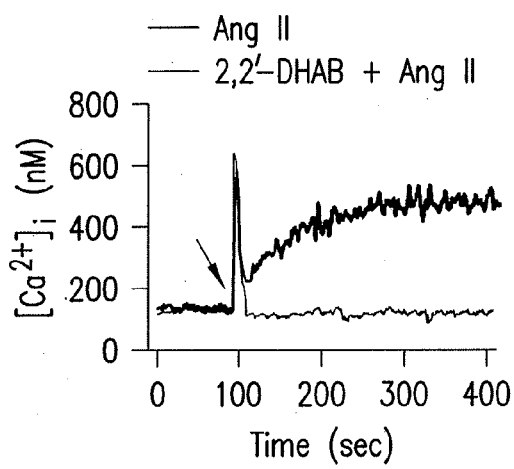
FIGS. 3A and 3B show the inhibition effects of 2,2'-DHAB on angiotensin II (Ang II) induced intracellular $Ca^{2+}$ ($[Ca^{2+}]_i$) increase and cADPR production in rat cardiomyocytes.
Figure 3B:
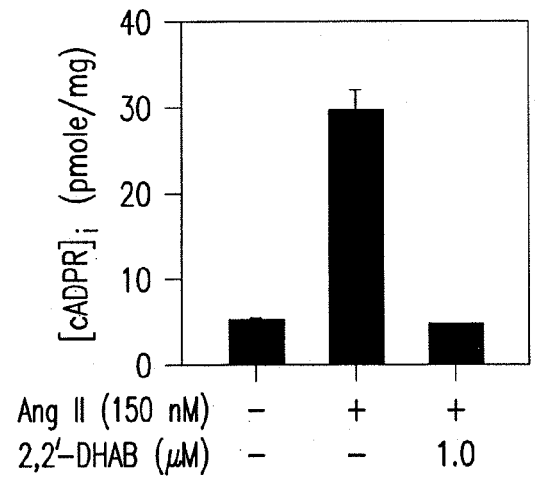

Cardiomyocytes were isolated from Sprague-Dawley rats, weighing 210-240 g, by the method with a slight modification [Xie et al., *Biochem. Biophys. Res. Commun.* (2005)330: 1290-8]. Rat hearts were rapidly excised, cannulated, and subjected to retrograde perfusion on a Langendorff apparatus at 37° C. with $Ca^{2+}$-free Krebs-Hanseleit (KH) buffer (10 mM HEPES, 118 mM NaCl, 4.7 mM KCl, 1.2 mM $MgSO_4$, 1.2 mM $KH_2PO_4$, 25 mM $NaHCO_3$, 10 mM pyruvate, 11 mM glucose, and 1 mM $CaCl_2$, pH 7.3) for 5 min and then with KH buffer containing 5 mM taurine, 0.075% collagenase Type II and 0.08 mg/l protease type XTV for 7-15 min and washed with KH buffer containing 0.2 mM $Ca^{2+}$. The left ventricle was removed, chopped into small pieces and further digested in a glass conical flask at 37° C. for 10 min with shaking. The undigested tissues were removed through a 200 mm-mesh nylon sheet. The $Ca^{2+}$ concentration in the cell preparation was gradually increased up to 1 mM. Isolated myocytes were pelleted by centrifugation at 60×g for 2 min at room temperature and resuspended in a stabilizing buffer (pH, 7.4) containing 20 mM HEPES, 137 mM NaCl, 4.9 mM KCl, 1.2 mM $MgSO_4$, 15 mM glucose, and 10 mM 2,3-butanedione monoxime (BDM). The cell preparation was kept in the stabilizing buffer containing 1% bovine serum albumin (BSA) at room temperature for 1.5 h and then washed three times with MEM medium at 37° C. The cells were attached on laminin coated confocal dishes were loaded with $Ca^{2+}$ indicator Fluo 3-AM and incubated for 20 min at 37° C. Changes in $[Ca^{2+}]_i$ in cardiomyocytes were determined at 488 nm excitation/530 nm emission by air-cooled argon laser system. The emitted fluorescence at 530 nm was collected using a photomultiplier. One image every 3 sec was scanned using confocal microscope. The results provided in FIG. 3. Ang II treatment in cardiomyocytes produced a rapid initial $Ca^{2+}$ peak and sustained $Ca^{2+}$ increase. Ang II-evoked sustained $Ca^{2+}$ increase but not initial $Ca^{2+}$ was significantly blocked by pretreatment with 1 mM 2,2-DHAB, which is a possible inhibitor of ADPR-cyclase.

Example 4

Measurement of OKT3-Mediated $[Ca^{2+}]_i$ Increase in Jurkat T Cells

Figure 4A:
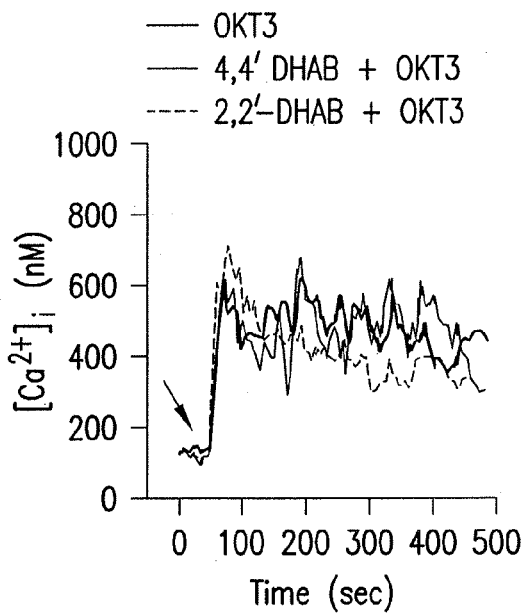
FIGS. 4A and 4B show the inhibition effects of 4,4'-DHAB or 2,2'-DHAB on OKT3, which is a ligand for CD3/TCR, induced $[Ca^{2+}]_i$ increase and cADPR production in Jurkat T cells.
Figure 4B:
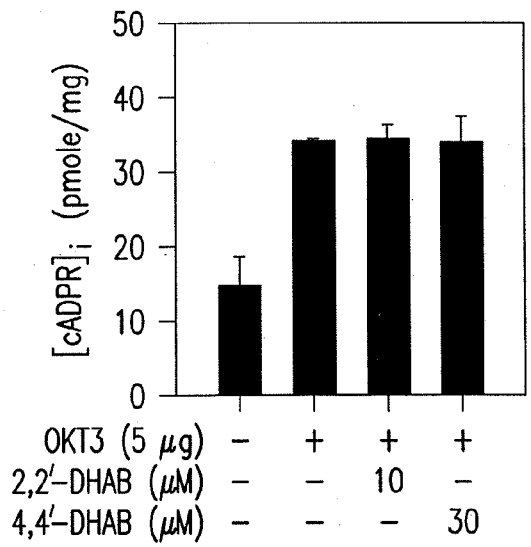

Changes in $[Ca^{2+}]_i$ in Jurkat T cells were determined as described above examples 1. The results provided in FIG. 4. Treatment of Jurkat T cells with OKT3 (5 mg/ml), which is a ligand for CD3/TCR, showed a typical biphasic increase of $[Ca^{2+}]_i$ an initial peak rise followed by a sustained rise. Pretreatment with 4,4'-DHAB as well as 2,2'-DHAB did not show any effects on OKT3-mediated $Ca^{2+}$ rise even at 10 mM (FIG. 4). These results obtained from in vitro study indicated that DHAB analogues are specific for the kidney or heart ADPR-cyclase.

Example 5

Measurement of Ang II-Induced Intracellular cADPR Concentration [cADPR]; in MMCs $[cADPR]_i$ was measured using a cyclic enzymatic assay as described previously [Graeff et al., *Biochem. J.* (2002)361: 379-84]. Aplysia californica ADPR-cyclase was purified from sea urchin egg according to the method described [Lee et al., *Cell Regul.* (1991)2:203-9]. Briefly, MMCs were treated with 0.3 ml of 0.6 M perchloric acid under sonication after Ang II treatment. Precipitates were removed by centrifugation at 20,000×g for 10 min. Perchloric acid was removed by mixing the aqueous sample with a solution containing 3 volumes of 1,1,2-trichlorotrifluoroethane to 1 volume of tri-n-octlyamine. After centrifugation for 10 min at 1500×g, the aqueous layer was collected and neutralized with 20 mM sodium phosphate (pH 8). To remove all contaminating nucleotides, the samples were incubated with the following hydrolytic enzymes overnight at 37° C.: 0.44 unit/ml nucleotide pyrophosphatase, 12.5 units/ml alkaline phosphatase, 0.0625 unit/ml NADase, and 2.5 mM $MgCl_2$ in 20 mM sodium phosphate buffer (pH 8.0). Enzymes were removed by filtration using Centricon-3 filters. To convert cADPR to $NAD^+$, the samples (0.1 ml/tube) were incubated with 50 ml of a cycling reagent containing 0.3 mg/ml Aplysia ADPR-cyclase, 30 mM nicotinamide, and 100 mM sodium phosphate (pH 8) at room temperature for 30 min. The samples were further incubated with the cycling reagent (0.1 ml) containing 2% ethanol, 100 mg/ml alcohol dehydrogenase, 20 mM resazurin, 10 mg/ml diaphorase, 10 mM riboflavin 5'-phosphate, 10 mM nicotinamide, 0.1 mg/ml BSA, and 100 mM sodium phosphate (pH 8.0) for 2 h at room temperature. An increase in the resorufin fluorescence was measured at 544 nm excitation and 590 nm emission using a fluorescence plate reader (Molecular Devices Corp., Spectra-Max GEMINI). Various known concentrations of cADPR were also included in the cycling reaction to generate a standard curve. The results provided in FIG. 2 and Table 1. These data show that 4,4'-DHAB inhibits cADPR production stimulated by Ang II in MMC at=5 nM and is far more potent in cell-based system than in vitro. Production of cADPR as well as later sustained $Ca^{2+}$ signal in response to Ang II was inhibited with different efficacy by these small molecules (Table 1). As expected, among these small molecules, DAHB showed the strongest inhibitory potency. The order of $IC_{50}$ was 4,4'-DAHB>resveratrol>azobenzene=piceatannol>2,2'-DAHB. These observations suggest that the biphenyl moiety but not the azo bond and position of hydroxyl group affect the binding of the inhibitor to the enzyme.

Example 6

Measurement of Ang II-Induced $[cADPR]_i$ in Cardiomyocytes

Measurement of $[cADPR]_i$ in cardiomyocytes were determined as described above examples 5. The results provided in FIG. 3. The production of cADPR was increased approximately 5 times more than control by Ang II in cardiomyocytes. Pretreatment with 2,2-DHAB inhibited the Ang II-mediated $[cADPR]_i$ in cardiomyocytes.

Example 7

Measurement of OKT3-Induced $[cADPR]_i$ in Jurkat T Cells

Measurement of $[cADPR]_i$ in Jurkat T cells were determined as described above examples 5. The results provided in FIG. 4. The production of cADPR was increased approximately 2 times more than control by OKT3 in Jurkat T cells. Pretreatment with 2,2'-DHAB or 4,4'-DHAB didn't inhibited the OKT3-mediated $[cADPR]_i$ in Jurkat T cells. These results indicate that DRAB analogues selectively inhibited kidney or heart ADPR-cyclase.

Example 8

Figure 5:
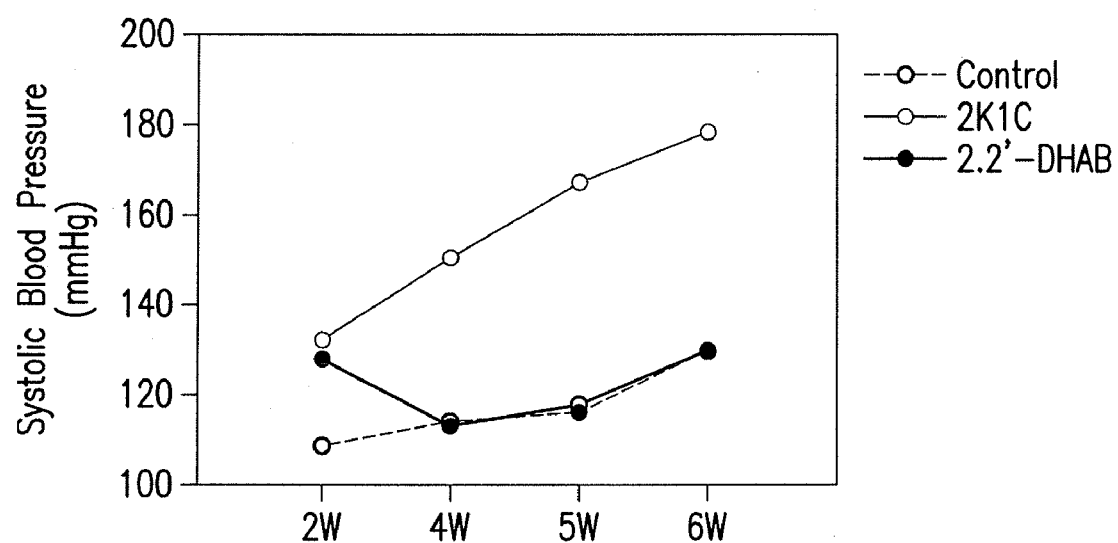
FIG. 5 is prevention effects of 2,2'-DHAB on systolic blood pressure in 2 kidney 1 clip hypertensive rat model.

Prevention Effect of 2,2'-DHAB on Elevation of Mean Arterial Blood Pressure in 2 Kidney 1 Clip Hypertensive Rat Model Renovascular hypertension was produced by 2KlC Sprague-Dawley male rats (7-9 weeks old) weighing 200 to 220-g were anesthetized with ketamine (100 mg/kg, intra-peritoneally) and rumpen (5 mg/kg, intraperitoneally). The left kidney was exposed through the median abdominal incision, and the renal artery was separated from the renal vein with caution. Then, a silver clip with 0.15 mm slit was placed around the renal artery. The sham procedure was performed, including the entire surgery with the exception of arterial clipping. To examine the effect of 2,2'-DHAB in the 2K1C model, we administered it at days 7 after the surgery for 7 weeks. 2,2'-DHAB was injected intraperitoneally with 58% DMSO plus saline at a dose of 1.5 µl/g body weight (428 µg/200 g/d). Sham group and control 2K1C received DMSO plus saline treatment. The dose of injected DMSO had no side effect on blood pressure (BP) or any other parameters. Systolic blood pressure was measured by a method using tail plethysmography in conscious rats once a week, from the day prior to surgery until the day of sacrifice. The results provided in FIG. 5 in which hypertensive control groups showed elevation of systolic blood pressure after 2 weeks but 2,2'-DHAB treated hypertensive groups prevented the elevation of blood pressure.

Example 9

Prevention Effect of 4,4'-DHAB on Diabetic Nephropathy in Diabetes Mouse Model

Male mice, weighing 20 25 g, were made diabetic by a single intravenous injection of STZ (65 mg/kg body weight) in 0.05 M citrate buffer (pH 4.8). At the same day, the control mice were injected with the citrate buffer. After 2 days, induction of diabetes was confirmed by tail blood glucose level measurement by using the LifeScan One Touch glucometer (Johnson & Johnson). The diabetic mice (>16 mM blood glucose) were randomly divided into two groups; 6 mice per group treated with vehicle (0.1% DMSO in saline, 100 µl) or DHAB (45 µg/kg body weight in 0.1% DMSO in saline, 100 µl) and resveratrol (45 µg/kg body weight in 0.1% DMSO in saline, 100 µl) administered by intraperitoneal injection once a day for 6 weeks. The control mice were 6 mice per group treated with the vehicle. On day 39, the mice were detained in individual metabolic cages for 24 h for urine collection. On day 42, the mice were anesthetized with diethyl ether, and blood samples were taken from the abdominal aorta. Bilateral kidneys were rapidly removed and weighed. Urine was gravimetrically collected, and urinary albumin concentrations were determined with an enzyme-linked immunosorbent assay using a murine microalbuminuria kit (Albuwell; Exocell, Philadelphia, Pa.). Urine and serum creatinine levels were measured using the QuantiChrom Creatinine Assay Kit (BioAssay Systems, Hayward, Calif.), following the manufacturer's protocol. The results provided in Table 2.

Below table 2 corresponds to Body weight, kidney weight, plasma glucose, creatinine clearance and urinary albumin in control (vehicle treated), diabetic and 4,4'-DHAB or resveratrol-treated diabetic mice.

TABLE 2

| | Control | STZ | 4,4'-DHAB | Resveratrol |
|---|---|---|---|---|
| Plasma glucose (mg/dl) | 134 ± 8.6 | 509 ± 95.3* | 342 ± 36.1* | 441 ± 48.7* |
| Body Weight (g) | 24.2 ± 0.65 | 20.9 ± 1.86* | 22.1 ± 0.58 | 22.6 ± 0.70 |
| Food intake (mg) | 0.67 ± 0.26 | 3.25 ± 0.85* | 2.27 ± 0.61* | 3.12 ± 0.79* |
| Water intake (ml) | 1.67 ± 1.15 | 12.00 ± 1.73* | 2.00 ± 1.73# | 5.67 ± 3.21# |
| Urine output (ml/day) | 1.22 ± 0.20 | 7.28 ± 1.98* | 2.27 ± 1.80# | 2.55 ± 2.09# |
| Urinary Albumin (µg/day) | 3.82 ± 3.40 | 11.68 ± 3.63* | 4.01 ± 3.61# | 2.97 ± 2.11# |
| Creatinine Clearance (ml/min/100 g) | 0.61 ± 0.17 | 3.90 ± 0.78* | 1.07 ± 1.02# | 0.91 ± 0.59# |

Data are expressed as mean SE; n = 6 mice per group.
*P < 0.05 vs. control;
P < 0.05 vs. STZ.

As shown in Table 2, administration of STZ to mice significantly enhanced the levels of blood glucose, urinary albumin, and creatinine clearance (CCr) compared to those in vehicle control mice. These data show the characteristics of diabetic renal dysfunction and establishment of diabetes mice. Moreover, treatment of diabetes mice with DHAB or resveratrol significantly recovered the urinary albumin, and CCr, but not the level of blood glucose, suggesting that bisphenyl analogues attenuate the progression of diabetic nephropathy, but not diabetes.

Other embodiments of the invention will be apparent to those skilled in the art from consideration of the specification and practice of the invention disclosed herein. It is intended that the specification and examples be indicated by the following claims.

The invention claimed is:

1. A method of treating a diabetic nephropathy by ADPR cyclase comprising administering a pharmaceutically acceptable composition comprising a therapeutically effective amount of a compound of the specific ADPR-cyclase inhibitor 4,4'-dihydroxyazobenzene.

2. The method of claim 1, wherein the pharmaceutically acceptable composition comprises the compound 4,4'-dihydroxyazobenzene in a concentration from about 0.0005 mM to about 50 mM.

* * * * *